(12) United States Patent
Leyrer et al.

(10) Patent No.: US 10,730,962 B2
(45) Date of Patent: Aug. 4, 2020

(54) RHEOLOGY MODIFIER

(71) Applicants: BASF SE, Ludwigshafen (DE);
HENKEL AG & CO. KGaA,
Düsseldorf (DE)

(72) Inventors: Reinhold Leyrer,
Dannstadt-Schauernheim (DE); Roland Ettl, Altlussheim (DE); Sabine Schuemann, Neuss (DE); Marouane Antir, Hilversum (NL); Thorsten Bastigkeit, Wuppertal (DE); Luca Bellomi, Düsseldorf (DE); Petra Woltery, Bergisch Gladbach (DE); Frank Sonnenschein, Haan (DE); Elisabeth Baumgarten, Duisburg (DE); Volker Blank, Leverkusen (DE)

(73) Assignees: BASF SE, Ludwingshafen (DE);
HENKEL AG & CO. KGAA,
Düsseldorf (DE)

( * ) Notice: Subject to any disclaimer, the term of this patent is extended or adjusted under 35 U.S.C. 154(b) by 257 days.

(21) Appl. No.: 15/527,968

(22) PCT Filed: Nov. 12, 2015

(86) PCT No.: PCT/EP2015/076442
§ 371 (c)(1),
(2) Date: May 18, 2017

(87) PCT Pub. No.: WO2016/079003
PCT Pub. Date: May 26, 2016

(65) Prior Publication Data
US 2017/0369602 A1    Dec. 28, 2017

(30) Foreign Application Priority Data

Nov. 18, 2014    (EP) .................................. 14193665

(51) Int. Cl.
| | | |
|---|---|---|
| *C08F 220/06* | (2006.01) | |
| *C08F 2/22* | (2006.01) | |
| *A61K 8/00* | (2006.01) | |
| *A61K 8/81* | (2006.01) | |
| *C08F 220/18* | (2006.01) | |
| *C11D 3/37* | (2006.01) | |
| *A61Q 19/00* | (2006.01) | |
| *C08F 6/02* | (2006.01) | |
| *C08F 251/02* | (2006.01) | |
| *C11D 1/12* | (2006.01) | |
| *C11D 1/722* | (2006.01) | |
| *C08F 220/28* | (2006.01) | |

(52) U.S. Cl.
CPC ............. *C08F 2/22* (2013.01); *A61K 8/8152* (2013.01); *A61Q 19/00* (2013.01); *C08F 6/02* (2013.01); *C08F 220/06* (2013.01); *C08F 220/18* (2013.01); *C08F 251/02* (2013.01); *C11D 1/12* (2013.01); *C11D 1/722* (2013.01); *C11D 3/3765* (2013.01); *A61K 2800/48* (2013.01); *C08F 220/28* (2013.01); *C08F 2800/20* (2013.01); *C08F 2810/10* (2013.01)

(58) Field of Classification Search
CPC .. C08F 2/22; C08F 6/02; C08F 220/06; C08F 220/18; C08F 251/02
USPC ........................................................ 524/457
See application file for complete search history.

(56) References Cited

U.S. PATENT DOCUMENTS

| | | |
|---|---|---|
| 3,087,828 A | 4/1963 | Linton |
| 3,415,758 A | 12/1968 | Powell et al. |
| 3,516,941 A | 6/1970 | Matson |
| 3,926,659 A | 12/1975 | Bernhard et al. |
| 4,146,403 A | 3/1979 | Armanini et al. |
| 4,192,691 A | 3/1980 | Armanini |
| 4,744,832 A | 5/1988 | Franz et al. |
| 5,227,446 A | 7/1993 | Denzinger et al. |
| 5,273,576 A | 12/1993 | Sullivan et al. |
| 5,433,779 A | 7/1995 | Deluca, Jr. |
| 5,456,749 A | 10/1995 | Iwasa et al. |
| 6,899,757 B2 | 5/2005 | Chang et al. |

FOREIGN PATENT DOCUMENTS

| | | | |
|---|---|---|---|
| CN | 1438253 A | 8/2003 | |
| DE | 4415623 A1 | 11/1995 | |
| EA | 201490702 A1 | 7/2014 | |
| EP | 0013836 A1 | 8/1980 | |
| EP | 0026914 A1 | 4/1981 | |
| EP | 0083781 A1 * | 7/1983 | ............... C08F 2/22 |
| EP | 0083781 A1 | 7/1983 | |
| EP | 0816404 A2 | 1/1998 | |
| RU | 2126019 C1 | 2/1999 | |
| WO | 1996014357 A1 | 5/1996 | |
| WO | 9926982 A1 | 6/1999 | |
| WO | 2001049817 A2 | 7/2001 | |
| WO | 2009019225 A2 | 2/2009 | |
| WO | WO-2009019225 A2 * | 2/2009 | ............ C08F 220/18 |
| WO | 2013138312 A1 | 9/2013 | |

* cited by examiner

*Primary Examiner* — Kelechi C Egwim
(74) *Attorney, Agent, or Firm* — Armstrong Teasdale LLP

(57) ABSTRACT

A rheology modifier obtainable by polymerizing (i) at least one ethylenically unsaturated carboxylic acid; (ii) at least one nonionic ethylenically unsaturated surfactant monomer, (iii) at least one $C_1$-$C_2$-alkyl methacrylate, and (iv) at least one $C_2$-$C_4$-alkyl acrylate, where the alkyl chain length averaged over the number of alkyl groups of the alkyl acrylate is 2.1 to 4.0. The polymerization is carried out in the presence of at least one hydrocarbon comprising at least one XH-group, wherein X is selected from the group consisting of O, P, N and S. Liquid formulations and particles containing liquid detergents comprising the rheology modifier are also described.

18 Claims, No Drawings

RHEOLOGY MODIFIER

CROSS-REFERENCE TO RELATED APPLICATIONS

This application is a U.S. National Phase Application of PCT/EP2015/076442, filed Nov. 12, 2015, which claims the benefit of priority to EP Application No. 14193665.8, filed Nov. 18, 2014, the contents of which are hereby expressly incorporated by reference in their entirety.

The present invention relates to a rheology modifier obtainable by polymerizing
(i) at least one ethylenically unsaturated carboxylic acid;
(ii) optionally at least one nonionic ethylenically unsaturated surfactant monomer,
(iii) at least one $C_1$-$C_2$-alkyl methacrylate, and/or
(iv) at least one $C_2$-$C_4$-alkyl acrylate, where the alkyl chain length averaged over the number of alkyl groups of the alkyl acrylate is 2.1 to 4.0;
in the presence of hydrocarbon comprising at least one XH-group, wherein X is selected from the group consisting of O, P, N and S. Further aspects of the invention are liquid formulations and especially particles containing liquid detergents comprising said rheology modifier.

In the commercial production of an aqueous polymer emulsion, or latex, or vinyl monomers, water soluble polymers are used as protective colloids in order to improve the rheological and stability characteristics of the emulsion (see e.g. WO 09/019225). Such emulsions are widely utilized in various applications including paints, binders, inks, paper, textiles, adhesives, floor polishes, and the like. Aqueous polymer emulsions are prepared by emulsion polymerization of vinyl monomers in the presence of stabilizers. The stability of the aqueous polymer emulsions is critically important during the polymerization reaction. Unstable polymer emulsions during polymerization will result in the high grit or coagulum in the final products. When this occurs, not only is there a certain amount of polymer loss, but the time and effort required in cleaning and filtering operations are an additional processing expense. Aqueous polymer emulsions used in certain applications, such as in liquid detergents like home and personal care formulations, require inclusion with the polymer emulsion of various ingredients such as fillers, microcapsules air bubbles and extenders, pigments, pH control agents, viscosity control agents, bactericides, antifoams, and the like. For a home and personal care formulation to develop its optimum cleaning function, storage stability and deposition of ingredients on the cleaned surface, the polymer emulsion particles must be well dispersed, swollen or dissolved in the formulation and develop its special structure so that the maximum polymer surface area and three-dimensional structure is available to fulfill all the customer requirements. If a polymer emulsion coagulates or agglomerates during the mixing of the formulation, the application properties of the final home and personal care formulations will be poor. Therefore not only the polymer emulsion itself must be colloidally stable or dissolved but also all the other ingredients in the home and personal care formulations to the mixing and other mechanical stresses involved in the production of the home and personal care formulations. The stability of aqueous polymer emulsions is obtained largely from the type of stabilizer system used in the manufacture of the polymer emulsion. Generally, the stabilizer system is introduced during the polymerization. Water-soluble polymers function as stabilizers for the preparation of aqueous polymer emulsions during the polymerization and are normally called protective colloids. A major class of protective colloids for use with vinyl monomers are starch and cellulose derivatives, which can be anchored at least partially to the polymer emulsion particle (see e.g. WO 99/026982). In the emulsion polymerization of ethylenically unsaturated monomers, the presence of an effective amount of starch and cellulose derivatives is known to produce latexes of submicron particle size having improved stability and performance (see e.g. WO 96/014357 or EP83781).

In certain applications, such as in liquid detergents like home and personal care formulations, the various ingredients such as surfactant, fillers, microcapsules, air bubbles, pigments, pH control agents, viscosity control agents, bactericides, antifoams, and the like have a tendency to creaming or sedimentation during storage for days, weeks or months. There is a need to stabilize these various ingredients in liquid detergents. In addition these liquid detergents like home and personal care formulations have to develop its optimum cleaning function, storage stability and deposition of perfect disperses ingredients like perfumes or softeners on the cleaned surface.

Thus, the objective of the present invention is to provide rheology modifiers that are able to improve the storage stability of liquid detergents.

It has now been found, surprisingly, that the mentioned objectives can be met to a great extent by a rheology modifier obtainable by polymerizing
(i) at least one ethylenically unsaturated carboxylic acid;
(ii) optionally at least one nonionic ethylenically unsaturated surfactant monomer,
(iii) at least one $C_1$-$C_2$-alkyl methacrylate, and/or
(iv) at least one $C_2$-$C_4$-alkyl acrylate, where the alkyl chain length averaged over the number of alkyl groups of the alkyl acrylate is 2.1 to 4.0;
in the presence of hydrocarbon comprising at least one XH-group, wherein X is selected from the group consisting of O, P, N and S.

In a preferred embodiment, the rheology modifier is obtainable by polymerizing
(i) at least one ethylenically unsaturated carboxylic acid;
(iii) at least one $C_1$-$C_2$-alkyl methacrylate, and/or
(iv) at least one $C_2$-$C_4$-alkyl acrylate, where the alkyl chain length averaged over the number of alkyl groups of the alkyl acrylate is 2.1 to 4.0;
in the presence of hydrocarbon comprising at least one XH-group, wherein X is selected from the group consisting of O, P, N and S.

In another preferred embodiment, the rheology modifier is obtainable by polymerizing
(i) at least one ethylenically unsaturated carboxylic acid;
(ii) at least one nonionic ethylenically unsaturated surfactant monomer,
(iii) at least one $C_1$-$C_2$-alkyl methacrylate, and/or
(iv) at least one $C_2$-$C_4$-alkyl acrylate, where the alkyl chain length averaged over the number of alkyl groups of the alkyl acrylate is 2.1 to 4.0;
in the presence of hydrocarbon comprising at least one XH-group, wherein X is selected from the group consisting of O, P, N and S.

The hydrocarbon according to the present invention comprise preferably at least one OH-group.

Hydrocarbons that can be used in accordance with the present invention can be naturally occurring hydrocarbons having at least one XH-group, wherein X is selected from the group consisting of O, P, N and S, e.g., casein, agarose, maltodextrin, alginic acid or its salts, fatty acids, cetyl alcohol, collagen, chitosan, lecithin, gelatin, albumin, polysaccharide such as starch, dextran, sucrose or cellulose.

Hydrocarbons that can be used in accordance with the present invention can be semi-synthetic hydrocarbons having at least one XH-group, wherein X is selected from the group consisting of O, P, N and S, e.g., chemically modified or substituted cellulose, such as celluloseester and -ether, celluloseacetate, ethylcellulose, hydroxypropylcellulose, hydroxypropylmethylcellulose, carboxymethylcellulose (CMC), derivatives of starch, starchether and -ester; water soluble modified cellulose, hydroxyethylcellulose, carboxymethylhydroxyethylcellulose or methylhydroxyethylcellulose.

Hydrocarbons that can be used in accordance with the present invention can be synthetic hydrocarbons having at least one XH-group, wherein X is selected from the group consisting of O, P, N and S, e.g., polymers with polyacrylate, polyvinylphosphate, polyvinylphosphonate, polyamide, polyvinylalcohol, polyvinylpyrrolidon (PVP) or water soluble polymers made from N-vinylamide and polyvinylpyrrolidon.

In a preferred embodiment, the hydrocarbons in accordance with the present invention are oligo- and/or polysaccharides which can be optionally substituted. Oligo- and polysaccharides are known in the art. An oligosaccharide is a saccharide polymer containing a small number (typically three to nine) of simple sugars (monosaccharides). Polysaccharides are polymeric carbohydrate molecules composed of long chains of monosaccharide units bound together by glycosidic linkages and on hydrolysis give the constituent monosaccharides or oligosaccharides. The oligo- and/or polysaccharides are present in an amount of less than 150 pphm (parts per hundred monomer), preferably in an amount of from 1 pphm to 150 pphm, more preferably in an amount of from 2 pphm to 75 pphm, most preferably in an amount of from 5 pphm to 50 pphm.

In a preferred embodiment, the polysaccharide in accordance with the present invention is a polymer of pyranose monomers, at least 30% of which monomers are in the α-anomeric conformation. A pyranose monomer is a monomer of a pyranose polysaccharide that is based upon a (tetrahydro)pyran ring like the tetrahydropyran

In polysaccharides, pyranose monomers are linked together by the formation of ether bonds involving an —OH group attached to a C-atom that is also attached to the O-atom of the (tetrahydro)pyran ring. This —OH group can be present in the cyclic monomer group in one of two conformations, namely the α- and the β-anomeric conformations (illustrated below by use of a particular "chair" conformation of the pyranose ring).

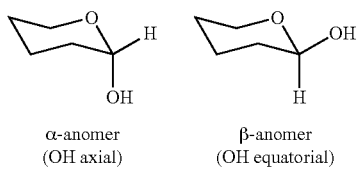

α-anomer
(OH axial)

β-anomer
(OH equatorial)

The C-atom in the above-depicted structures to which the two O-atoms are attached is called the anomeric carbon, and also represents a chiral centre when the molecule is locked in the ring conformation. In this respect, it is to be noted that the formation of the ring is reversible in aqueous solution for pyranose monomers, due to interconversion of the molecules between linear (hydroxyaldehyde) and cyclic (hemiacetal) forms.

The α-anomeric conformation in a polysaccharide is illustrated below by reference to the structure of amylose (which is used as an illustrative example only).

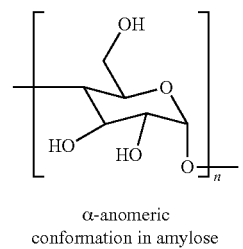

α-anomeric
conformation in amylose

In amylose, the ether bonds are formed between the 1- and 4-positions of pyranose monomer (i.e. between the anomeric carbon and the C-atom in the 4-position in the ring relative to that carbon). Such linkages are described as α(1→4). However, the polysaccharides employed in the first aspect of the invention may contain any ether linkages found in polysaccharides derived from natural sources, such as α(1→6), β(1→4) and/or β(1→6), provided that less than 50% of the pyranose monomers are present in the α-anomeric conformation. In a preferred embodiment, the hydrocarbon is a starch, like corn starch, potato starch, wheat starch, tapioca starch and soluble starch.

In a more preferred embodiment, the hydrocarbons of the present invention are one or more of amylose, amylopectin, agarose and agaropectin; a mixture of amylose and amylopectin; or a mixture of agarose and agaropectin.

In another preferred embodiment, the hydrocarbons are β-1,4-D-glucopyranosides which may be optionally substituted. The, β-1,4-D-glucopyranosides are present in an amount of less than 150 pphm (parts per hundred monomer), preferably in an amount of from 1 pphm to 150 pphm, more preferably in an amount of from 2 pphm to 75 pphm, most preferably in an amount of from 5 pphm to 50 pphm.

In an even more preferred embodiment, the hydrocarbons are carboxymethylcellulose (CMC) and/or starch. Carboxymethylcellulose (CMC) is present in an amount of less than 150 pphm (parts per hundred monomer), preferably in an amount of from 1 pphm to 150 pphm, more preferably in an amount of from 2 pphm to 75 pphm, most preferably in an amount of from 5 pphm to 50 pphm. In a further preferred embodiment, starch is present in an amount of less than 150 pphm (parts per hundred monomer), preferably in an amount of from 1 pphm to 150 pphm, more preferably in an amount of from 2 pphm to 75 pphm, most preferably in an amount of from 5 pphm to 50 pphm.

If CMC and starch are present, CMC is present in an amount less than 90 pphm (parts per hundred monomer), preferably in an amount of from 1 pphm to 50 pphm, most preferably in an amount of from 3 pphm to 35 pphm and starch is present in an amount of less than 60 pphm (parts per hundred monomer), preferably in an amount of from 1 pphm to 25 pphm, most preferably in an amount of from 2 pphm to 15 pphm.

The ethylenically unsaturated carboxylic acid is generally a monoethylenically unsaturated mono- or dicarboxylic acid having 3 to 8 carbon atoms. Suitable ethylenically unsaturated carboxylic acids are selected, for example, from acrylic acid, methacrylic acid, itaconic acid and maleic acid. Of these, methacrylic acid is particularly preferred.

Nonionic ethylenically unsaturated surfactant monomers which are suitable as monomer ii) are known per se. These are, for example,
(a) urethane-group-containing reaction products of a monoethylenically unsaturated isocyanate and nonionic surfactants,
(b) esters of ethylenically unsaturated carboxylic acids and nonionic surfactants,
(c) vinyl or allyl ethers of nonionic surfactants.

Suitable nonionic surfactants are preferably alkoxylated $C_6$-$C_{30}$-alcohols, such as fatty alcohol alkoxides or oxo alcohol alkoxides. At least 2, e.g. 2 to 100, preferably 3 to 20, mol of at least one $C_2$-$C_4$-alkylene oxide are used per mole of alcohol. Different alkylene oxide units can be arranged blockwise or be present in random distribution. Preferably, the alkylene oxide used is ethylene oxide and/or propylene oxide.

A further class of suitable nonionic surfactants is alkylphenol ethoxides with $C_6$-$C_{14}$-alkyl chains and 5 to 30 mol of ethylene oxide units.

In preferred embodiments, the nonionic ethylenically unsaturated surfactant monomer has the general formula (I)

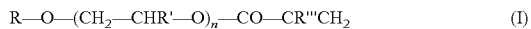

$$R-O-(CH_2-CHR'-O)_n-CO-CR'''CH_2 \quad (I)$$

in which R is $C_6$-$C_{30}$-alkyl, preferably $C_8$-$C_{22}$-alkyl, more preferably $C_{16}$-$C_{22}$-alkyl R' is hydrogen or methyl, preferably hydrogen,
R" is hydrogen or methyl, preferably methyl, and
n is an integer from 2 to 100, preferably 3 to 50, more preferably 25.

The repeat units in the brackets are derived from ethylene oxide or propylene oxide. The meaning of R' is independent in each repeat unit from other repeat units. Different alkylene oxide units can be arranged blockwise or be present in random distribution.

Suitable $C_1$-$C_2$-alkyl methacrylates are methyl methacrylate and ethyl methacrylate, of which methyl methacrylate is particularly preferred.

Suitable $C_2$-$C_4$-alkyl acrylates are ethyl acrylate, n-propyl acrylate and n-butyl acrylate. The type and amount of the $C_2$-$C_4$-alkyl acrylates are chosen such that a certain alkyl chain length averaged over the number of alkyl groups of the $C_2$-$C_4$-alkyl acrylate units is established, as stated above. The average alkyl chain length is calculated by multiplying the number of carbons in the longest alkyl chain of the alkyl radical (i.e. for example 2 for ethyl and 4 for n-butyl) by the molar fraction of the alkyl acrylate of the total amount of the $C_2$-$C_4$-alkyl acrylates, and adding the individual contributions.

Preferably, the $C_2$-$C_4$-alkyl acrylate comprises at least n-butyl acrylate, in particular a mixture of n-butyl acrylate with ethyl acrylate. Preferably, the copolymer comprises 5 to 85% by weight, based on the total weight of the copolymer, of copolymerized units of n-butyl acrylate, where a range from more than 10% by weight to 60% by weight is preferred and a range from 15% by weight to 45% by weight is particularly preferred.

Ethylenically polyunsaturated monomers that can be used are, for example, ethylene glycol di(meth)acrylate, 1,6-hexanediol di(meth)acrylate, divinylbenzene and the like.

The rheology modifier may further comprise an anionic and/or a nonionic emulsifier.

Typical emulsifiers are anionic emulsifiers, such as, for example, sodium lauryl sulfate, sodium tridecyl ether sulfates, dioctyl sulfosuccinate sodium salt and sodium salts of alkylaryl polyether sulfonates; and nonionic emulsifiers, such as, for example, alkylaryl polyether alcohols and ethylene oxide-propylene oxide copolymers.

Preferred emulsifiers have the general formula (II)

$$R-O-(CH_2-CHR'-O)_n-X \quad (II)$$

in which R is $C_6$-$C_{30}$-alkyl,
R' is hydrogen or methyl,
X is hydrogen or $SO_3M$,
M is hydrogen or an alkali metal, and
n is an integer from 2 to 100.

In a preferred embodiment, the hydrocarbons comprising at least one XH-group in accordance with the present invention are present in an amount of 1 to 100% by weight, preferably 1 to 50% by weight, more preferably 5 to 50% by weight, even more preferably 5 to 20% by weight, based on the total weight of the copolymer. That is, given that the hydrocarbons comprising at least one XH-group are not grafted into the copolymer, if the hydrocarbons comprising at least one XH-group are present, e.g., in an amount of 100% based on the total weight of the copolymer, both components (i.e. the hydrocarbons comprising at least one XH-group on the one hand and the copolymer on the other hand) are present in a ratio of 1:1 by weight.

The rheology modifier of the present invention can be prepared in various ways, preferably by emulsion polymerization.

For the polymerization, a suitable polymerization initiator is used. Thermally activatable free-radical polymerization initiators are preferred.

Suitable thermally activatable free-radical initiators are primarily those of the peroxy and azo type. These include, inter alia, hydrogen peroxide, peracetic acid, t-butyl hydroperoxide, di-t-butyl peroxide, dibenzoyl peroxide, benzoyl hydroperoxide, 2,4-dichlorobenzoyl peroxide, 2,5-dimethyl-2,5-bis(hydroperoxy)hexane, perbenzoic acid, t-butyl peroxypivalate, t-butyl peracetate, dilauroyl peroxide, dicapryloyl peroxide, distearoyl peroxide, dibenzoyl peroxide, diisopropyl peroxydicarbonate, didecyl peroxydicarbonate, dieicosyl peroxydicarbonate, di-t-butyl perbenzoate, azobisisobutyronitrile, 2,2'-azobis-2,4-dimethylvaleronitrile, ammonium persulfate, potassium persulfate, sodium persulfate and sodium perphosphate.

The persulfates (peroxodisulfates), in particular sodium persulfate, are most preferred.

While carrying out the emulsion polymerization, the initiator is used in an adequate amount to initiate the polymerization reaction. The initiator is usually used in an amount of from about 0.005 to 3% by weight, based on the total weight of the monomers used. The amount of initiator is preferably about 0.02 to 2% by weight and in particular 0.05 to 0.5% by weight, based on the total weight of the monomers used.

The emulsion polymerization usually takes place at 35 to 100° C. It can either be carried out as a batch process or else in the form of a feed method. Preference is given to the feed procedure in which at least some of the polymerization initiator and, if appropriate, some of the monomers are initially introduced and heated to the polymerization temperature, and then the remainder of the polymerization mixture is introduced via a plurality of separate feeds, of which one or more comprise the monomers in pure or emulsified form, continuously or stepwise while maintaining the polymerization. Preferably, the monomer feed takes place in the form of a monomer emulsion. In parallel to the monomer feed, a further polymerization initiator can be metered in.

In preferred embodiments, the entire amount of initiator is initially introduced, i.e. no further metered addition of initiator takes place in parallel to the monomer feed. It has surprisingly been found that this procedure leads to particularly high transparency of the rheology modifier.

In a preferred embodiment, therefore, the thermally activatable free-radical polymerization initiator is initially introduced in its entirety, and the monomer mixture, preferably in the form of a monomer emulsion, is run in. Before the monomer mixture feed is started, the initial charge is brought to the activation temperature of the thermally activatable free-radical polymerization initiator or to a higher temperature. The activation temperature is regarded as being the temperature at which at least half the initiator has disintegrated after one hour.

According to another preferred type of preparation, the rheology modifier of the present invention is obtained through polymerization of a monomer mixture in the presence of a redox initiator system. A redox initiator system comprises at least one oxidizing agent component and at least one reducing agent component, where, in the reaction medium, preferably heavy metal ions are additionally present as catalyst, for example cerium salts, manganese salts or iron(II) salts.

Suitable oxidizing agent components are, for example, peroxides and/or hydroperoxides, such as hydrogen peroxide, tert-butyl hydroperoxide, cumene hydroperoxide, pinane hydroperoxide, diisopropylphenyl hydroperoxide, dicyclohexyl percarbonate, dibenzoyl peroxide, dilauroyl peroxide and diacetyl peroxide. Hydrogen peroxide and tert-butyl hydroperoxide are preferred.

Suitable reducing agent components are alkali metal sulfites, alkali metal dithionites, alkali metal hyposulfites, sodium hydrogensulfite, sodium hydroxymethansulfinate, mono- and dihydroxyacetone, sugars (e.g. glucose or dextrose), ascorbic acid and its salts, acetone bisulfite adduct and/or an alkali metal salt of hydroxymethanesulfinic acid. Ascorbic acid is preferred.

Also suitable as reducing agent component or catalyst are iron(II) salts, such as, for example, iron(II) sulfate, tin(II) salts, such as, for example, tin(II) chloride, titanium(III) salts, such as titanium(III) sulfate.

The use amounts of oxidizing agent are 0.001 to 5.0% by weight, preferably from 0.005 to 1.0% by weight and particularly preferably from 0.01 to 0.5% by weight, based on the total weight of the monomers used. Reducing agents are used in amounts of from 0.001 to 2.0% by weight, preferably from 0.005 to 1.0% by weight and particularly preferably from 0.01 to 0.5% by weight, based on the total weight of the monomers used.

A particularly preferred redox initiator system is the system sodium peroxodisulfate/ascorbic acid, e.g. 0.001 to 5.0% by weight of sodium peroxodisulfate and 0.001 to 2.0% by weight of ascorbic acid, in particular 0.005 to 1.0% by weight of sodium peroxodisulfate and 0.005 to 1.0% by weight of ascorbic acid, particularly preferably 0.01 to 0.5% by weight of sodium peroxodisulfate and 0.01 to 0.5% by weight of ascorbic acid.

A further particular redox initiator system is the system t-butyl hydroperoxide/hydrogen peroxide/ascorbic acid, e.g. 0.001 to 5.0% by weight of t-butyl hydroperoxide, 0.001 to 5.0% by weight of hydrogen peroxide and 0.001 to 2.0% by weight of ascorbic acid, in particular 0.005 to 1.0% by weight of t-butyl hydroperoxide, 0.005 to 1.0% by weight of hydrogen peroxide and 0.005 to 1.0% by weight of ascorbic acid, particularly preferably 0.01 to 0.5% by weight of t-butyl hydroperoxide, 0.01 to 0.5% by weight of hydrogen peroxide and 0.01 to 0.5% by weight of ascorbic acid.

In a preferred embodiment, a monomer mixture, preferably in the form of a monomer emulsion, is run into an aqueous initial charge which is heated to the polymerization temperature. In parallel to the monomer feed, at least times, an oxidizing agent component and a reducing agent component of the redox initiator system are run in. Preferably, some of the oxidizing agent component of the redox initiator system is initially introduced. If appropriate, some of the monomers can be initially introduced.

The rheology modifier of the present invention can be subjected to a chemical deodorization. During the chemical deodorization, a further initiator, e.g. a redox initiator, is added after the end of the actual emulsion polymerization. Redox initiators suitable for the chemical deodorization comprise, as oxidizing component, for example at least one organic peroxide and/or hydroperoxide, such as hydrogen peroxide, tert-butyl peroxide, cumene hydroperoxide, pinane hydroperoxide, diisopropylphenyl hydroperoxide, dibenzoyl peroxide, dilauroyl peroxide and diacetyl peroxide and, as reducing component, for example iron(II) salts, alkali metal sulfites, ascorbic acid, acetonebisulfite adduct and/or an alkali metal salt of hydroxymethanesulfinic acid.

The copolymer dispersion generally has a solids content of from 25 to 40% by weight, in particular about 30% by weight.

In unneutralized form, the rheology modifier has a relatively low viscosity. It is therefore easy to handle and can be metered or circulated by pumping without problems. As a result of neutralization, e.g. to a pH of more than 5.5, preferably more than 6, in particular 8 to 10, the rheology modifier becomes soluble and the viscosity of the aqueous medium increases considerably. Suitable neutralizing agents are, for example, sodium hydroxide, potassium hydroxide, ammonium hydroxide, amines, such as triethylamine, triethanolamine, monoethanolamine, and other alkaline materials.

The rheology modifiers according to the invention are suitable as rheology modifiers in coating compositions, formulations for the manufacture of textiles, for textile printing pastes, in the pharmaceutical and cosmetics sector, for paints, pigments, in food and for home care and personal care products like detergents, liquid soaps, shampoos, shower gels, cleaners and liquid detergents.

The viscosity of the liquid detergents or cleaners can be measured by means of customary standard methods (for example Brookfield viscometer LVT-II at 20 rpm and 20° C., spindle 3) and is preferably in the range from 100 to 5000 mPas. Preferred compositions have viscosities of from 300 to 4000 mPas, with values between 1000 and 2000 mPas being particularly preferred.

The present invention also relates to a liquid formulation comprising the rheology modifier as defined in any one of claims 1 to 10 and at least one component selected from the group consisting of gas bubbles, nanoparticles, microcapsules made of or with active, enzymes, perfumes, pharmaceuticals, organic particles, pigments, fibers, biocides, herbicides, and fungicides.

Particles, vesicles and gas bubbles can be stably dispersed in the home care and personal care products, in particular aqueous liquid detergents, comprising the rheology modifier of the present invention. Stable means that for example the liquid detergents comprising the rheology modifier of the present invention are stable at room temperature and at 40° C. over a period of at least 6 weeks and preferably of at least 12 weeks without creaming up or sedimenting or at 50° C. over a period of at least 4 week, preferably at least 3 months without creaming up or sedimenting.

A preferred embodiment of an inventive liquid formulation is a liquid detergent composition, comprising
- at least one rheology modifier of this invention, preferably as defined in any of the claims 1 to 10,
- at least one surfactant,
- a liquid continuous phase comprising water and
- at least one component, dispersed in said liquid continuous phase.

The term dispersion according to the invention is defined in DIN EN ISO 862: 1995-10. A continuous phase is defined as the dispersion medium, in which said component is dispersed.

A compound is considered a liquid, if it is in the liquid state at 20° C., 1013 mbar.

A compound is considered a solid, if it is in the solid state at 20° C., 1013 mbar.

All above mentioned preferred embodiments of the rheology modifier of this invention are mutatis mutandis preferred for said liquid detergent composition of this embodiment. A preferred total amount of rheology modifier of this invention is from 0.1 to 1 wt. %, more preferably from 0.2 to 0.9 wt. % and more preferably from 0.4 to 0.9 wt. %, based on the total weight of the composition.

Preferably, the continuous phase comprises the rheology modifier of the invention.

The total amount of surfactant is preferred from 3 to 30 wt. %, more preferred 4 to 22 wt. %, and most preferred 4 to 18 wt. %, based on the total weight of the composition.

A particularly preferred liquid detergent composition of this embodiment comprises at least one anionic surfactant.

Suitable anionic surfactants comprise alkylbenzenesulfonic acid salts, olefinsulfonic acid salts, $C_{12}$-$C_{18}$ alkanesulfonic acid salts, salts of sulfuric acid monoesters with a fatty alcohol, a fatty acid soap, salts of sulfuric acid monoesters with an ethoxylated fatty alcohol or a mixture of two or more of these anionic surfactants. Among these anionic surfactants, alkylbenzenesulfonic acid salts, fatty acid soaps, salts of sulfuric acid monoesters with an ethoxylated fatty alcohol and mixtures thereof are more preferred.

The total amount of anionic surfactant is preferably from 2 to 20 wt. %, more preferred 3 to 15 wt. %, in each case relative to the entire liquid washing or cleaning agent.

Surfactants of the sulfonate type which may here preferably be considered are $C_{9-13}$ alkylbenzenesulfonates, olefinsulfonates, i.e. mixtures of alkenesulfonates and hydroxyalkanesulfonates and disulfonates, as are obtained, for example, from $C_{12-18}$ monoolefins with a terminal or internal double bond by sulfonation with gaseous sulfur trioxide and subsequent alkaline or acidic hydrolysis of the sulfonation products. $C_{12-11}$ alkanesulfonates and the esters of α-sulfofatty acids (ester sulfonates), for example the α-sulfonated methyl esters of hydrogenated coconut, palm kernel or tallow fatty acids, are also suitable.

Preferred alk(en)ylsulfates are the salts of sulfuric acid semi-esters of $C_{12}$-$C_{18}$ fatty alcohols for example prepared from coco fatty alcohol, tallow fatty alcohol, lauryl, myristyl, cetyl or stearyl alcohol or $C_{10}$-$C_{20}$ oxo alcohols and those semi-esters of secondary alcohols of these chain lengths. $C_{12}$-$C_{16}$ alkylsulfates and $C_{12}$-$C_{15}$ alkylsulfates and $C_{14}$-$C_{15}$ alkylsulfates are preferred because of their washing characteristics. 2,3-Alkylsulfates are also suitable anionic surfactants.

The sulfuric acid monoesters of straight-chain or branched $C_{7-21}$ alcohols ethoxylated with 1 to 6 mol of ethylene oxide are also suitable, such as 2-methyl-branched $C_{9-11}$ alcohols with on average 3.5 mol ethylene oxide (EO) or $C_{12-18}$ fatty alcohols with 1 to 4 EO.

Fatty acid soaps are further suitable anionic surfactants. Saturated and unsaturated fatty acid soaps are in particular suitable, such as the salts of lauric acid, myristic acid, palmitic acid, stearic acid, (hydrogenated) erucic acid and behenic acid and in particular soap mixtures derived from natural fatty acids, for example coconut, palm kernel, olive oil or tallow fatty acids.

The anionic surfactants including the fatty acid soaps may be present in the form of the sodium, potassium, magnesium or ammonium salts thereof. The anionic surfactants are preferably present in the form of the sodium or ammonium salts thereof. Amines usable for neutralization are preferably choline, triethylamine, monoethanolamine, diethanolamine, triethanolamine, methylethylamine or a mixture thereof, wherein monoethanolamine is preferred.

A particularly preferred liquid detergent composition of this embodiment comprises at least one anionic surfactant and at least one nonionic surfactant.

Suitable nonionic surfactants include alkoxylated fatty alcohols, alkoxylated fatty acid alkyl esters, fatty acid amides, alkoxylated fatty acid amides, polyhydroxyfatty acid amides, alkylphenol polyglycol ethers, amine oxides, alkyl polyglucosides and mixtures thereof.

Preferably used alkoxylated fatty alcohols are ethoxylated, in particular primary alcohols with preferably 8 to 18 C atoms and on average 4 to 12 mol ethylene oxide (EO) per mol alcohol, in which the alcohol residue is linear. In particular, alcohol ethoxylates with 12 to 18 C atoms, for example prepared from coconut, palm, tallow fat or oleyl alcohol, and on average 5 to 8 EO per mol of alcohol are preferred. Preferred ethoxylated alcohols include, for example, $C_{12}$-$C_{14}$ alcohols with 4 EO or 7 EO, $C_{9-11}$ alcohol with 7 EO, $C_{12-18}$ alcohols with 5 EO or 7 EO and mixtures of these. The stated degrees of ethoxylation are statistical averages which, for a specific product, may be an integer or a fractional number. Preferred alcohol ethoxylates have a narrow homologue distribution (narrow range ethoxylates, NRE). In addition to these nonionic surfactants, fatty alcohols with more than 12 EO may also be used. Examples of these are tallow fatty alcohol with 14 EO, 25 EO, 30 EO or 40 EO. Nonionic surfactants containing EO and PO groups together in one molecule may also be used according to the invention. A mixture of a (relatively highly) branched ethoxylated fatty alcohol and an unbranched ethoxylated fatty alcohol, such as for example a mixture of a $C_{16-18}$ fatty alcohol with 7 EO and 2-propylheptanol with 7 EO, is furthermore suitable.

The total amount of nonionic surfactants is preferably 1 to 20 wt. %, more preferably 3 to 15 wt. %, particularly preferred 1 to 10 wt. %, most preferred 1 to 7 wt. %, in each case relative to the entire quantity of liquid detergent composition.

A particularly preferred embodiment of said liquid formulation is a liquid detergent composition, comprising relative to the entire quantity of liquid detergent composition
- at least one rheology modifier of this invention, preferably as defined in any of the claims 1 to 10,
- 2 to 20 wt. % (more preferably 3 to 15 wt. %) of at least one anionic surfactant, 1 to 10 wt. % (more preferably 1 to 7 wt. %) of at least one nonionic surfactant a liquid continuous phase comprising water and at least one component, dispersed in said liquid continuous phase.

In another embodiment of said liquid detergent composition it is preferred to add at least one inorganic salt. An inorganic salt according to the invention is composed out of an anion and a cation, both being inorganic. Inorganic means, that the ions of said salt comprise no hydrogen atom, which has a direct covalent bond to a carbon atom.

Said inorganic salt is comprised in a preferred amount of 0.1 to 1 wt. % (more preferably 0.2 to 0.9 wt. %, most preferred from 0.1 to 0.7 wt. %) in each case relative to the entire quantity of liquid detergent composition.

Preferred inorganic salts are selected from inorganic salts of monovalent metal cations. Sodium chloride, sodium sulfate, potassium chloride, potassium sulfate or mixtures thereof are particularly preferred.

A preferred embodiment of said liquid formulation is a liquid detergent composition, comprising at least one rheology modifier of this invention, preferably as defined in any of the claims 1 to 10, at least one surfactant (preferred at least one anionic surfactant and at least on nonionic surfactant), at least one inorganic salt, a liquid continuous phase comprising water and at least one component, dispersed in said liquid continuous phase.

A particularly preferred embodiment of said liquid formulation is a liquid detergent composition, comprising relative to the entire quantity of liquid detergent composition 0.1 to 1 wt. % (more preferably from 0.4 to 0.9 wt. %) of at least one rheology modifier of this invention, preferably as defined in any of the claims 1 to 10, 2 to 20 wt. % (more preferably 3 to 15 wt. %) of at least one anionic surfactant, 1 to 10 wt. % (more preferably 1 to 7 wt. %) of at least one nonionic surfactant 0.1 to 1 wt. % (more preferably 0.2 to 0.9 wt. %) of at least one inorganic salt, a liquid continuous phase comprising water and at least one component, dispersed in said liquid continuous phase.

The liquid detergent composition comprises in general a liquid continuous phase comprising water and at least one component, dispersed in said liquid continuous phase.

A preferred component dispersed in said liquid phase are particles of a particulate solid.

Preferred particles of a particulate solid have an average particle size $X_{50,3}$ from 0.01 to 2000 µm, especially from 0.05 to 500 µm, preferably from 1 to 150 µm, particularly preferred from 5 to 150 µm, more preferred from 5 to 100 µm, most preferred from 10 to 100 µm, even more preferably from 10 to 80 µm. Said particle size can be determined by laser diffraction.

Said particles of a particulate solid are particularly chosen from agglomerates, granules, capsules, pigments, fibers or mixtures thereof. Agglomerates, granules, capsules, pigments or mixtures thereof are particularly preferred, whereas capsules and/or pigments (especially particularly preferred microcapsules and/or effect pigments) are most preferred dispersed components in said liquid detergent composition.

Capsules are core-shell-particles, comprising a solid shell which envelopes a core. The core is preferably a liquid. Capsules and microcapsules are known in the art. The average particle size $X_{50,3}$ of particularly well suited capsules or microcapsules are 0.05 to 500 µm, particularly preferred from 5 to 150 µm, most preferred from 10 to 100 µm, for example 10 to 80 µm.

Particularly suited capsules have a bulk density of 0.80 to 1.20 g/cm$^3$, especially preferred of 0.90 to 1.10 g/cm$^3$ (according to ISO 697:1981).

Preferred capsules, especially microcapsules, used in the liquid detergent composition are water insoluble microcapsules. Said water insoluble capsules, especially microcapsules, comprise a shell material, which does not dissolve or disintegrate in water at least at a temperature between 20 and 40° C. Water insoluble capsules, especially microcapsules, are advantageous, because they will not disrupt during the wash and allow disruption of the shell and the release of the core after the wash under mechanical stress.

Preferred capsules, especially microcapsules, comprise at least one material selected from polyurethane, polyolefine, polyamide, polyester, polysaccharide, epoxide resin, silicon resin, reaction product of carbonyl compounds (preferably formaldehyde) with compounds with NHgroups (preferably melamin or urea or mixture) in its shell.

The preparation of capsules, especially microcapsules, is known. Suitable methods are disclosed in U.S. Pat. Nos. 3,516,941, 3,415,758 or in EP 0 026 914 A1. One method is the acid induced condensation reaction of melamin-formaldehyde-prepolymers (and/or their C1-4-alkylethers) in a medium comprising water and a dispersed phase of the core material. Further microcapsules suitable for this invention are described in WO 2001/049817 A2.

The shell may comprise at least one compound bearing at least one cationic charge. Preferred cationic compounds in the shell are cationic polymers. Preferred cationic polymers are selected from Polyquaternium 7, Polyquaternium-10, Polyquaternium-11, Polyquaternium-16, Polyquaternium-55, Polyquaternium-69 ore mixtures thereof.

The shell surrounding the core of the capsules, especially microcapsules, has a preferred mean thickness from 0.01 and 50 µm, particularly preferred from 0.1 µm to 30 µm, most preferred from 0.5 µm to 8 µm.

The core of the capsules, especially microcapsules, comprises preferably an active ingredient, suitable for use for textiles. Such active ingredient is preferably selected from (a) scent, (b) actives for fibre care, especially silicon oils, solubilized cationic polymers, (c) skin care actives (especially vitamin E, aloe vera extract, green tea extract, D-panthenol, plankton extract, urea and/or glycin).

Most preferred, the dispersed compound comprise perfume microcapsules, with at least one scent in the core. The preferred embodiments of the microcapsules are of course also mutatis mutandis preferred embodiments of said perfume microcapsule.

In another preferred embodiment, the component dispersed in the liquid continuous phase are particles of a particulate solid, which are preferably pigments. The pigments in accordance with the present invention are effect pigments or nacreous pigments. Nacreous pigments produce pearl-like, metallic and iridescent effects. Natural pearl essence, a mixture of guanine and hypoxanthine obtained from the scales of fish has long been used in cosmetic formulations. Synthetic nacreous pigments developed for cosmetic and liquid detergents use include mica-based pigments and bismuth oxychloride, or bismuth oxychloride mica. Muscovite mica platelets coated with a metallic oxide, such as titanium dioxide have been widely used. A relatively thin titanium dioxide coating produces a pearl-like or silvery luster. Mica platelets with thicker coatings produce color, even though the components are colorless, through the phenomenon of light interference; they are known as interference pigments. Platy pigments are also composed of a plurality of laminar platelets coated with one or more reflecting/transmitting layers. Typically, effect pigments are a laminar platy substrate such as natural mica or glass flake that has been coated with a metal oxide layer.

A description of effect pigments' properties can be found in the Pigment Handbook, Volume I, Second Edition, pp. 829-858, John Wiley & Sons, NY 1988. If colorless metal oxides are used to coat the laminar platy substrate, effect pigments exhibit pearl-like luster as a result of reflection and refraction of light, and depending on the thickness of the metal oxide layer, they can also exhibit interference color effects. If colored metal oxides are used, the observed effects depend on reflection, refraction and absorption.

The color, called the reflection color, is seen most effectively by specular or mirror-like reflection, where the angle of reflection equals the angle of incidence. The reflection color is a function of optical thickness, i.e. the geometrical thickness times the refractive index, of the coating. Optical thickness of about 100 nm to about 160 nm produce reflection which may be called white, silvery or pearly; optical thickness of about 190 nm or more produce colored reflections. Nacreous or pearlescent pigments containing mica or mica coated with titanium dioxide are known in the art. Reference is made, e.g., to U.S. Pat. Nos. 3,087,828; 3,926,659; 4,146,403; 4,192,691; 4,744,832; 5,273,576; 5,433,779; 5,456,749; 6,899,757; WO 2013/138312.

BASF CHIONE™ MSVA is a performance mineral composed of Synthetic Fluorophlogopite, commonly known as synthetic mica, coated with lauroyl lysine. The resulting powder is very white and have a velvety texture, which can enhance the optical brightness and the feel of both anhydrous, hydroalcoholic or pure aqueous formulations. This highly brilliant additive is suitable for all cosmetic or home and personal cleaning applications, including eye and lip area or liquid detergents use. It has without coloured additives a very white appearance in both anhydrous or aqueous formulations.

Especially preferred pigments stabilised by the rheology modifier of the present invention are the white Chione™ HD Infinite White 5130V or the larger coloured pigment Flamenco Sparkle Gold 220J or Multi Reflections™ Soft Sparkle Orchid 580P or Reflecks™ Pearlescent and Iridescent Pigment based on Borsilicate and $TiO_2$ like Glimmers of Green G830L or Shiny rouge G450D based on Borsilicate and $Fe_2O_3$ or Purely Purple G536L based on Borsilicate and $TiO_2$ and Ferric Ferrocyanide or Varying Violet G580D based on Borsilicate and $TiO_2$ and $SiO_2$ from BASF.

Particularly suited pigments have a bulk density of 80 to 900 kg/m$^3$, especially preferred of 100 to 600 g/cm$^3$ (according to ISO 697:1981).

The average particle size $X_{50,3}$ of particularly well suited pigments is 0.05 to 200 μm, particularly preferred from 5 to 150 μm, most preferred from 10 to 100 μm, for example 10 to 80 μm.

The rheology modifier of the present invention can also modify the surface of the pigments in such a way, that the surface tension of the pigments are adopted to the aqueous formulation and the stability of the pigment in the aqueous formulation is enhanced, so that sedimentation or creaming of the pigments during longer storage times are avoided. The rheology modifier of the present invention is specially adopted to the surface coating of the above-mentioned pigments so that the interaction energies between the pigment surface, the rheology modifier and the aqueous formulation is minimised, thus leading to the enhanced stability of the total formulation.

In one embodiment of the present invention, the rheology modifier as provided and as to be employed as described herein is obtainable by copolymerizing ethylacrylate (e.g., 30-40 pphm), (n-)butylacrylate (e.g., 30-40 pphm), and methacrylic acid (e.g., 25-35 pphm) as also exemplified herein. Optionally, further compounds such as Lutensol AT 25 Methacrylate (cf. ASSOC Table 1 below), carboxymethylcellulose with 150 mPas at 20 rpm (cf. CMC150 in Table 1 below), an emulsifier (e.g., SDS), 2-ethylhexyl thioglycolate, $H_2O_2$, NaPS, and/or C12-alkyldiphenyloxide disulfonate (cf. Table 1 below) may be added to the polymerization reaction. In a further embodiment, a further additive, particularly a (metal) complexing agent such as Trilon B (e.g., up to 0.3 pphm) (cf. Table 1 below) and/or a chain transfer agent like, e.g., 2-EHTG (cf. Table 1 below), may be added in order to regulate the viscosity.

If the component, which is dispersed in the liquid continuous phase, comprises pigments as particles of a particulate solid, it was found to be a preferred option to choose a rheology modifier, which is obtainable by copolymerizing ethylacrylate (e.g., 30-40 pphm), (n-)butylacrylate (e.g., 30-40 pphm), and methacrylic acid (e.g., 25-35 pphm) as also exemplified herein. Optionally, further compounds such as Lutensol AT 25 Methacrylate (cf. ASSOC Table 1 below), carboxymethylcellulose with 150 mPas at 20 rpm (cf. CMC150 in Table 1 below), an emulsifier (e.g., SDS), 2-ethylhexyl thioglycolate, $H_2O_2$, NaPS, and/or C12-alkyldiphenyloxide disulfonate (cf. Table 1 below) may be added to the polymerization reaction. In a further embodiment, a further additive, particularly a (metal) complexing agent such as Trilon B (e.g., up to 0.3 pphm) (cf. Table 1 below) and/or a chain transfer agent like, e.g., 2-EHTG (cf. Table 1 below), may be added in order to regulate the viscosity.

In one embodiment, the rheology modifier according to the present invention (particularly in context with particles/pigments as described herein) is obtainable by adding 30-40 pphm ethylacrylate, 30-40 pphm n-butylacrylate, 25-35 pphm methacrylic acid, 0.2-2 pphm 60% Lutensol AT 25 Methacrylate (cf. ASSOC Table 1 below), and 8-20 pphm carboxymethylcellulose with 150 mPas at 20 rpm (cf. CMC150 in Table 1 below) and optionally further compounds such as, e.g., an emulsifier (e.g., SDS), 2-ethylhexyl thioglycolate, $H_2O_2$, NaPS, and/or C12-alkyldiphenyloxide disulfonate (cf. Table 1 below) to the polymerization reaction. In a further embodiment, a further additive, particularly a (metal) complexing agent such as Trilon B (e.g., up to 0.3 pphm) (cf. Table 1 below) and/or a chain transfer agent like, e.g., 2-EHTG (cf. Table 1 below), may be added in order to regulate the viscosity.

Said preferred rheology modifier is most preferably used for stabilization of pigments in the liquid continuous phase, if said pigments have
 i) a bulk density of 80 to 900 kg/m$^3$, especially preferred of 100 to 600 g/cm$^3$ (according to ISO 697:1981) and/or
 ii) an average particle size $X_{50,3}$ of 5 to 150 μm, most preferred from 10 to 100 μm, for example 10 to 80 μm.

A preferred embodiment of said liquid formulation is a liquid detergent composition, comprising
 at least one rheology modifier of this invention, preferably as defined in any of the claims 1 to 10,
 at least one surfactant (preferred at least one anionic surfactant and at least on nonionic surfactant),
 at least one inorganic salt,
 a liquid continuous phase comprising water and at least one microcapsule and/or pigment, dispersed in said liquid continuous phase.

A particularly preferred embodiment of said liquid formulation is a liquid detergent composition, comprising relative to the entire quantity of liquid detergent composition
0.1 to 1 wt. % (more preferably from 0.4 to 0.9 wt. %) of at least one rheology modifier of this invention, preferably as defined in any of the claims 1 to 10,
2 to 20 wt. % (more preferably 3 to 15 wt. %) of at least one anionic surfactant,
1 to 10 wt. % (more preferably 1 to 7 wt. %) of at least one nonionic surfactant
0.1 to 1 wt. % (more preferably 0.2 to 0.9 wt. %) of at least one inorganic salt,
a liquid continuous phase comprising water and
at least one microcapsule and/or pigment, dispersed in said liquid continuous phase.

The liquid detergent composition of the invention is preferably prepared by a method, comprising the steps
i) adjusting the temperature of an aqueous liquid to a temperature of 20 to 60° C.,
ii) adding the surfactants while mixing,
iii) adding the rheology modifier of the invention while mixing,
iv) cooling the resulting mixture to at most 40° C., preferably to at most 35° C.,
iv) adding the compound to be dispersed in the continuous phase and dispersing said compound,
v) cooling down to ambient temperature,
whereas
at least said steps are performed in said order,
said method may comprise any optional steps before, between or after steps i) to v).

The present invention further relates to the use of the rheology modifier as defined above to stabilize particles such as gas bubbles, nanoparticles, microcapsules made of or with active, enzymes, perfumes, pharmaceuticals, organic particles, pigments, fibers, biocides, herbicides, and fungicides in a liquid detergent.

The following examples illustrate the invention. However, the present invention is not limited to the embodiments described in the examples.

EXAMPLES

TABLE 1

| Abbreviations: | |
|---|---|
| EA | Ethylacrylate |
| BA | n-Butylacrylate |
| EHA | Ethylhexylacrylate |
| MAS | Methacrylic acid |
| AS | Acrylic acid |
| AM | Acrylamide |
| ASSOC | 60% Lutensol AT 25 Methacrylate [=(C16-18)-(EO)25-Methacrylate, 20% Methacrylic acid, 20% water] |
| PETIA | Pentaerythritol tri/tetraacrylate |
| BDA2 | Butandioldiacrylate |
| Maltodextrin | Watersoluble mixture obtained by hydrolysis of starch (Poly-α-glucose) |
| CMC80 | Carboxymethylcellulose with 80 mPas at 20 rmp |
| CMC150 | Carboxymethylcellulose with 150 mPas at 20 rpm |
| CMC230 | Carboxymethylcellulose with 230 mPas at 20 rpm |

TABLE 1-continued

| Abbreviations: | |
|---|---|
| PVP | Poly(1-vinyl-2-pyrrolidone) with viscosity of 20 mPas at 20% aqueous solution |
| 2-EHTG | 2-Ethylhexyl thioglycolate |
| SDS | Sodium lauryl sulfate |
| C12-Alkyldiphenyloxide disulfonate | benzene,1,1'-oxybis, tetrapropylene derivatives, sulfonated, sodium salts |
| Sodium lauryl ether sulfate | Sodium lauryl ether sulphate with critical micel concentration of 0.38 g |
| NaPS | Sodiumperoxodisulfate |
| H2O2 | Hydrogen peroxide |
| PVP4 | Poly(1-vinyl-2-pyrrolidone) with viscosity of 3.7 mPas at 20% aqueous solution |
| Flamenco | Flamenco Sparkle Gold 220J |
| Chione | Chione ™ HD Infinite White S130V |
| Trilon B | Tetrasodium ethylenediaminetetraacetate |

Comparative Example V1.1—Production of a Rheology Modifier in the Absence of a Hydrocarbon In a stirring apparatus consisting of a 4 liter HWS vessel with anchor agitator reflux condenser, inside thermo sensor and metering station, 850.2 g deionized water, 0.66 g emulsifier SDS (15% in water) and 52.0 g PVP were mixed. At 85° C. 1.86 g NaPS (7% in water) were added and the mixture was stirred at 85° C. for 5 minutes. For 2 hours an emulsion consisting of 213.56 g deionized water, monomers (78.0 g methacrylic acid, 175.5 g ethylacrylate, 8.13 g ASSOC, 7.8 g emulsifier SDS (15% in water), and 2.89 g emulsifier C12-Alkyldiphenyloxide disulfonate (45% in water)) were added and constantly stirred at 85° C. After complete addition of the emulsion 13.94 g deionized water was added. After 15 minutes following the addition of the emulsion 26 g $H_2O_2$ (1% in water) and 10.4 g ascorbic acid (1% in water) were added at a constant rate for 2 hours and 15 minutes to the mixture. Then 0.13 g ethylenediaminetetraacetic acid ferric potassium com (4% in water) was added. Subsequently the reaction mixture was cooled slowly to room temperature. During cooling 26 g $H_2O_2$ (1% in water) and 39 g ascorbic acid (1% in water) were added at a constant rate for 1 hour. An aqueous polymer dispersion with 21% solid content was obtained.

Comparative Example V1.2—Production of a Rheology Modifier in the Absence of a Hydrocarbon In a stirring apparatus consisting of a 4 liter HWS vessel with anchor agitator, reflux condenser, inside thermo sensor and metering station, 898.23 g deionized water, 2.72 g emulsifier sodium lauryl ether sulfate (28% in water) were mixed. At 75° C. 8.71 g NaPS (7% in water) were added and the mixture was stirred at 75° C. for 5 minutes. For 2 hours an emulsion consisting of 184.37 g deionized water, monomers (22.88 g acrylic acid, 45.75 g acrylamide, 228.75 g n-butylacrylate, 38.13 g ASSOC and 13.62 g emulsifier Sodium lauryl ether sulfate (28% in water)) were added and constantly stirred at 75° C. After complete addition of the emulsion 14.64 g deionized water was added. For another 1 hour at 75° C. further polymerization took place. Subsequently 0.15 g ethylenediaminetetraacetic acid ferric potassium complex (1% in water) and 6.1 g $H_2O_2$ (5% in water) were added to the mixture. Then 15.25 g sodium hydroxymethansulfinate (1% in water) was added for 1 hour at 75° C. Subsequently the reaction mixture was cooled slowly to room temperature. An aqueous polymer dispersion with 21% solid content was obtained.

Comparative Example V1.3—Production of a Rheology Modifier in the Absence of a Hydrocarbon In a stirring apparatus consisting of a 4 liter HWS vessel with anchor agitator, reflux condenser, inside thermo sensor and metering station, 844.12 g deionized water, 2.72 g emulsifier sodium lauryl ether sulfate (28% in water) were mixed. At 75° C. 32.68 g NaPS (7% in water) were added and the mixture was stirred at 75° C. for 5 minutes. For 2 hours an emulsion consisting of 184.37 g deionized water, monomers (22.88 g acrylic acid, 122 g acrylamide, 95.31 g n-butylacrylate, 95.31 g ethylacrylate, 38.13 g ASSOC and 13.62 g emulsifier sodium lauryl ether sulfate (28% in water)) were added and constantly stirred at 75° C. After complete addition of the emulsion 14.64 g deionized water was added. For another 1 hour at 75° C. further polymerization took place. Subsequently 0.15 g ethylenediaminetetraacetic acid ferric potassium complex (1% in water) and 6.1 g $H_2O_2$ (5% in water) were added to the mixture. Then 15.25 g sodium hydroxymethansulfinate (1% in water) was added for 1 hour at 75° C. Subsequently the reaction mixture was cooled slowly to room temperature. An aqueous polymer dispersion with 21% solid content was obtained.

Comparative Example V2.2—Production of a Rheology Modifier in the Absence of a Hydrocarbon In a stirring apparatus consisting of a 4 liter HWS vessel with anchor agitator reflux condenser, inside thermo sensor and metering station, 701.48 g deionized water, 2.8 g emulsifier SDS (15% in water) were mixed. At 85° C. 2 g NaPS (7% in water) were added and the mixture was stirred at 85° C. for 5 minutes. For 2 hours an emulsion consisting of 229.88 g deionized water, monomers (84 g methacrylic acid, 94.5 g n-butylacrylate, 94.5 g ethylacrylate, 8.75 g ASSOC, 8.4 g emulsifier SDS (15% in water), and 3.11 g emulsifier C12-Alkyldiphenyloxide disulfonate (45% in water)) were added and constantly stirred at 85° C. After 15 minutes following the addition of the emulsion 28 g $H_2O_2$ (1% in water) and 11.2 g ascorbic acid (1% in water) were added at a constant rate for 2 hours and 15 minutes to the mixture. After complete addition of the emulsion 15.12 g deionized water was added. Then 0.14 g ethylenediaminetetraacetic acid ferric potassium complex (4% in water) was added. Subsequently the reaction mixture was cooled slowly to room temperature. During cooling 28 g $H_2O_2$ (1% in water) and 42 g ascorbic acid (1% in water) were added at a constant rate for 1 hour. An aqueous polymer dispersion with 21% solid content was obtained.

Comparative Example V2.3—Production of a Rheology Modifier in the Absence of a Hydrocarbon In a stirring apparatus consisting of a 4 liter HWS vessel with anchor agitator, reflux condenser, inside thermo sensor and metering station, 651.92 g deionized water, 0.69 g emulsifier SDS (15% in water) were mixed. At 85° C. 1.86 g NaPS (7% in water) were added and the mixture was stirred at 85° C. for 5 minutes. For 2 hours an emulsion consisting of 215.2 g deionized water, monomers (78 g methacrylic acid, 182 g ethylacrylate, 7.8 g emulsifier SDS (15% in water), and 2.89 g emulsifier C12-Alkyldiphenyloxide disulfonate (45% in water)) were added and constantly stirred at 85° C. After complete addition of the emulsion 13.94 g deionized water was added. After 15 minutes following the addition of the emulsion 26 g $H_2O_2$ (1% in water) and 10.4 g ascorbic acid (1% in water) were added at a constant rate for 2 hours and 15 minutes to the mixture. Then 0.13 g ethylenediaminetetraacetic acid ferric potassium complex (4% in water) was added. Subsequently the reaction mixture was cooled slowly to room temperature. During cooling 26 g $H_2O_2$ (1% in water) and 39 g ascorbic acid (1% in water) were added at a constant rate for 1 hour. An aqueous polymer dispersion with 21% solid content was obtained.

Example B1.4—Production of a Rheology Modifier with CMC

In a stirring apparatus consisting of a 4 liter HWS vessel with anchor agitator, reflux condenser, inside thermo sensor and metering station, 847.55 g deionized water, 0.69 g emulsifier SDS (15% in water) and 52 g CMC150 were mixed. The following steps of the process were identical to the process described in Comparative Example V2.3: At 85° C. 1.86 g NaPS (7% in water) were added and the mixture was stirred at 85° C. for 5 minutes. For 2 hours an emulsion consisting of 215.2 g deionized water, monomers (78 g methacrylic acid, 182 g ethylacrylate, 7.8 g emulsifier SDS (15% in water), and 2.89 g emulsifier C12-Alkyldiphenyloxide disulfonate (45% in water)) were added and constantly stirred at 85° C. After complete addition of the emulsion 13.94 g deionized water was added. After 15 minutes following the addition of the emulsion 26 g $H_2O_2$ (1% in water) and 10.4 g ascorbic acid (1% in water) were added at a constant rate for 2 hours and 15 minutes to the mixture. Then 0.13 g ethylenediaminetetraacetic acid ferric potassium complex (4% in water) was added. Subsequently the reaction mixture was cooled slowly to room temperature. During cooling 26 g $H_2O_2$ (1% in water) and 39 g ascorbic acid (1% in water) were added at a constant rate for 1 hour. An aqueous polymer dispersion with 21% solid content was obtained.

Example B1.11—Production of a Rheology Modifier with CMC

In a stirring apparatus consisting of a 4 liter HWS vessel with anchor agitator, reflux condenser, inside thermo sensor and metering station, 806.82 g deionized water, 2.8 g emulsifier SDS (15% in water) and 28 g CMC150 were mixed. The following steps of the process were identical to the process described in Comparative Example V2.2: At 85° C. 2 g NaPS (7% in water) were added and the mixture was stirred at 85° C. for 5 minutes. For 2 hours an emulsion consisting of 229.88 g deionized water, monomers (84 g methacrylic acid, 94.5 g n-butylacrylate, 94.5 g ethylacrylate, 8.75 g ASSOC, 8.4 g emulsifier SDS (15% in water), and 3.11 g emulsifier C12-Alkyldiphenyloxide disulfonate (45% in water)) were added and constantly stirred at 85° C. After 15 minutes following the addition of the emulsion 28 g $H_2O_2$ (1% in water) and 11.2 g ascorbic acid (1% in water) were added at a constant rate for 2 hours and 15 minutes to the mixture. After complete addition of the emulsion 15.12 g deionized water was added. Then 0.14 g ethylenediaminetetraacetic acid ferric potassium complex (4% in water) was added. Subsequently the reaction mixture was cooled slowly to room temperature. During cooling 28 g H$_2$O$_2$ (1% in water) and 42 g ascorbic acid (1% in water) were added at a constant rate for 1 hour. An aqueous polymer dispersion with 21% solid content was obtained.

Examples B1.1 to B1.3, B1.5 to B1.10, B1.12 and B1.13 were produced via the same process except that the amount of the starting material was varied as can be derived from Table 2.

Example B2.1—Production of a Rheology Modifier with CMC

In a stirring apparatus consisting of a 4 liter HWS vessel with anchor agitator, reflux condenser, inside thermo sensor and metering station, 882.14 g deionized water, 0.14 g ethylenediaminetetraacetic acid ferric potassium complex (4% in water), 2.8 g emulsifier SDS (15% in water) and 28 g CMC150 were mixed. At 85° C. 2 g NaPS (7% in water) were added and the mixture was stirred at 85° C. for 5 minutes. For 2 hours an emulsion consisting of 229.99 g deionized water, monomers (84 g methacrylic acid, 96.6 g n-butylacrylate, 96.6 g ethylacrylate, 3.5 g ASSOC, 8.4 g emulsifier SDS (15% in water), and 3.11 g emulsifier C12-Alkyldiphenyloxide disulfonate (45% in water)) were added and constantly stirred at 85° C. 11.2 g ascorbic acid (0.25% in water) was added in 2 hours and 30 minutes. After 15 minutes following the addition of the emulsion 0.56 g H$_2$O$_2$ (1% in water) was added. After complete addition of the emulsion 15.01 g deionized water was added. Subsequently the reaction mixture was cooled slowly to room temperature. During cooling 1.12 g H$_2$O$_2$ (1% in water) and 21 g ascorbic acid (1% in water) were added at a constant rate for 1 hour. An aqueous polymer dispersion with 21% solid content was obtained.

Example B2.2 was produced via the same process except that the amount of the starting material was varied as can be derived from Table 2.

Example B3.1—Production of a Rheology Modifier with CMC and Starch

In a stirring apparatus consisting of a 4 liter HWS vessel with anchor agitator, reflux condenser, inside thermo sensor and metering station, 740.52 g deionized water, 0.17 g ethylenediaminetetraacetic acid ferric potassium complex (4% in water), 1.21 g emulsifier sodium lauryl ether sulfate (28% in water), 68 g maltodextrin (50% in water) and 17 g CMC150 were mixed. At 85° C. 2.43 g NaPS (7% in water) were added and the mixture was stirred at 85° C. for 5 minutes. For 2 hours an emulsion consisting of 279.28 g deionized water, monomers (102 g methacrylic acid, 114.75 g n-butylacrylate, 114.75 g ethylacrylate, 10.63 g ASSOC, 13.96 g emulsifier sodium lauryl ether sulfate (28% in water)) were added and constantly stirred at 85° C. 13.6 g ascorbic acid (0.25% in water) was added in 2 hours and 30 minutes. After 15 minutes following the addition of the emulsion 0.68 g H$_2$O$_2$ (1% in water) was added. After complete addition of the emulsion 10.91 g deionized water and 8.49 g NaPS (1% in water) were added during 10 minutes. Subsequently the reaction mixture was cooled slowly to room temperature. During cooling 1.36 g H$_2$O$_2$ (1% in water) and 25.5 g ascorbic acid (2% in water) were added at a constant rate for 2 hour. An aqueous polymer dispersion with 26% solid content was obtained.

Examples B3.2 to B3.5 were produced via the same process except that the amount of the starting material was varied as can be derived from Table 2.

Example B4.1—Production of a Rheology Modifier with Starch

In a stirring apparatus consisting of a 4 liter HWS vessel with anchor agitator, reflux condenser, inside thermo sensor and metering station, 644.46 g deionized water, 2.46 g emulsifier sodium lauryl ether sulfate (28% in water) and 184 g maltodextrin (50% in water) were mixed. At 85° C. 18.4 g NaPS (1% in water) were added and the mixture was stirred at 85° C. for 5 minutes. For 2 hours an emulsion consisting of 339.99 g deionized water, monomers (126.5 g methacrylic acid, 143.75 g n-butylacrylate, 143.75 g ethylacrylate, 57.5 g ASSOC, 22.18 g emulsifier sodium lauryl ether sulfate (28% in water) 73.6 g NaPS (1% in water)) were added and constantly stirred at 75° C. After complete addition of the emulsion 18.4 g deionized water was added. For another 1 hour at 85° C. further polymerization took place. Subsequently 0.92 g ethylenediaminetetraacetic acid ferric potassium complex (1% in water) and 9.2 g H$_2$O$_2$ (5% in water) were added to the mixture. Then 23 g sodium hydroxymethansulfinate (1% in water) was added for 1 hour at 85° C. Subsequently the reaction mixture was cooled slowly to room temperature. An aqueous polymer dispersion with 31% solid content was obtained.

Example B4.2—Production of a Rheology Modifier with CMC

In a stirring apparatus consisting of a 4 liter HWS vessel with anchor agitator, reflux condenser, inside thermo sensor and metering station, 1473.3 g deionized water, 0.92 g ethylenediaminetetraacetic acid ferric potassium complex (1% in water), 4.6 g emulsifier SDS (15% in water) and 55.2 g CMC150 were mixed. At 85° C. 3.29 g NaPS (7% in water) were added and the mixture was stirred at 85° C. for 5 minutes. For 2 hours an emulsion consisting of 229.88 g deionized water, monomers (138 g methacrylic acid, 159.85 g n-butylacrylate, 159.85 g ethylacrylate, 2.88 g ASSOC, 13.8 g emulsifier SDS (15% in water) and 5.11 g C12-Alkyldiphenyloxide disulfonate (45% in water) were added and constantly stirred at 85° C. After complete addition of the emulsion 24.66 g deionized water was added. After 15 minutes following the addition of the emulsion 0.92 g H$_2$O$_2$ (25% in water) and 18.4 g ascorbic acid (0.25% in water) added in 2 hours and 15 minutes. Then 1.84 g H$_2$O$_2$ (25% in water) were added. Subsequently the reaction mixture was cooled slowly to room temperature. During cooling 46 g ascorbic acid (2% in water) were added at a constant rate for 2 hour. An aqueous polymer dispersion with 21% solid content was obtained.

Example B2.2 was produced via the same process except that the amount of the starting material was varied as can be derived from Table 2.

Example B5.1—Production of a Rheology Modifier with High CMC Content

In a stirring apparatus consisting of a 4 liter HWS vessel with anchor agitator, reflux condenser, inside thermo sensor and metering station, 1240.6 g deionized water, 0.71 g emulsifier sodium lauryl ether sulfate (28% in water) and 100 g CMC80 were mixed. At 90° C. 1.43 g NaPS (7% in water) were added and the mixture was stirred at 85° C. for 5 minutes. For 3 hours an emulsion consisting of 226.66 g deionized water, monomers (80 g methacrylic acid, 60 g n-butylacrylate, 60 g ethylacrylate, 8 g PETIA (5% in 1,2-propandiole, 13.57 g emulsifier sodium lauryl ether sulfate (28% in water) were added and constantly stirred at 90° C. For 3 hours were simultaneously added 90 g NaPS (1% in Water). After complete addition of the emulsion and NaPS 10.72 g deionized water was added. For another 0.5 hour at 90° C. further polymerization took place. Subsequently the reaction mixture was cooled slowly to room temperature. At 90° C. 0.8 g $H_2O_2$ (25% in water) were added and during cooling 20 g ascorbic acid (2% in water) were added at a constant rate for 2 hours. An aqueous polymer dispersion with 16% solid content was obtained.

Examples B5.2, B5.7, B5.8, B5.9, B5.10, B5.11, B5.13, B5.14, B5.15, B5.16, B5.18, B5.19, B5.21 were produced via the same process except that the amount of the chemical ingredients were varied as can be derived from Table 2.

Example B5.3—Production of a Rheology Modifier with High CMC Content

In a stirring apparatus consisting of a 4 liter HWS vessel with anchor agitator, reflux condenser, inside thermo sensor and metering station, 1070.1 g deionized water, 0.54 g emulsifier sodium lauryl ether sulfate (28% in water) and 75 g CMC150 were mixed. At 75° C. 6.43 g NaPS (7% in water) were added and the mixture was stirred at 75° C. for 5 minutes. For 2 hours an emulsion consisting of 94.56 g deionized water, monomers (60 g methacrylic acid, 44.63 g n-butylacrylate, 44.63 g ethylacrylate, 0.94 g ASSOC, 10.18 g emulsifier sodium lauryl ether sulfate (28% in water) were added and constantly stirred at 75° C. After complete addition of the emulsion 8.04 g deionized water was added. For another 1 hour at 75° C. further polymerization took place. Subsequently the reaction mixture was cooled slowly to room temperature. At 75° C. 0.6 g $H_2O_2$ (25% in water) were added and during cooling 15 g ascorbic acid (2% in water) were added at a constant rate for 2 hours. An aqueous polymer dispersion with 16% solid content was obtained.

Examples B5.4, B5.12, B5.20 were produced via the same process except that the amount of the chemical ingredients were varied as can be derived from Table 2.

Example B5.5—Production of a Rheology Modifier with CMC

In a stirring apparatus consisting of a 4 liter HWS vessel with anchor agitator, reflux condenser, inside thermo sensor and metering station, 1927.6 g deionized water, 1.2 g ethylenediaminetetraacetic acid ferric potassium complex (1% in water), 6 g emulsifier SDS (15% in water) and 72 g CMC150 were mixed. At 90° C. 4.29 g NaPS (7% in water) were added and the mixture was stirred at 90° C. for 5 minutes. For 2 hours an emulsion consisting of 492.84 g deionized water, monomers (180 g methacrylic acid, 208.5 g n-butylacrylate, 208.5 g ethylacrylate, 3.75 g ASSOC, 18 g emulsifier SDS (15% in water), and 6.67 g emulsifier C12-Alkyldiphenyloxide disulfonate (45% in water)) were added and constantly stirred at 90° C. After 15 minutes following the addition of the emulsion 1.2 g $H_2O_2$ (1% in water) were added and 18 g ascorbic acid (0.25% in water) were simultaneously added for 2 hours and 30 minutes. After complete addition of the emulsion 32.16 g deionized water was added. After complete addition of the ascorbic acid (0.25% in water) the reaction mixture was cooled slowly to room temperature. At 90° C. 2.4 g $H_2O_2$ (25% in water) were added and during cooling 60 g ascorbic acid (2% in water) were added at a constant rate for 2 hours. An aqueous polymer dispersion with 21% solid content Examples B5.6, B5.17 were produced via the same process except that the amount of the chemical ingredients were varied as can be derived from Table 2.

Example B5.22—Production of a Rheology Modifier with CMC

In a stirring apparatus consisting of a 4 liter HWS vessel with anchor agitator, reflux condenser, inside thermo sensor and metering station, 1474.3 g deionized water, 0.92 g ethylenediaminetetraacetic acid ferric potassium complex (1% in water), 4.6 g emulsifier SDS (15% in water), 1.15 g Trilon B (tetrasodium ethylenediaminetetraacetate) and 55.2 g CMC150 were mixed. At 85° C. 3.29 g NaPS (7% in water) was added and the mixture was stirred at 85° C. for 5 minutes. For 2 hours an emulsion consisting of 377.84 g deionized water, monomers (138 g methacrylic acid, 159.85 g n-butylacrylate, 159.85 g ethylacrylate, 2.88 g ASSOC, 13.8 g emulsifier SDS (15% in water) and 5.11 g C12-Alkyldiphenyloxide disulfonate (45% in water) were added and constantly stirred at 85° C. After complete addition of the emulsion 24.66 g deionized water was added. After 15 minutes following the addition of the emulsion 0.92 g $H_2O_2$ (25% in water) was added and 18.4 g ascorbic acid (0.25% in water) was added in 2 hours and 15 minutes. Then 1.84 g $H_2O_2$ (25% in water) was added. Subsequently the reaction mixture was cooled slowly to room temperature. During cooling 46 g ascorbic acid (2% in water) was added at a constant rate for 2 hours. An aqueous polymer dispersion with 21% solid content was obtained.

TABLE 2

Summary of Examples

| Example | Monomers (pphm) | | | | | Other components (pphm) | | | | | | |
|---|---|---|---|---|---|---|---|---|---|---|---|---|
| | EA | BA | EHA | MAS | AM | ASSOC | Malto-dextrin | CMC150 | PVP | 2-EHTG | SDS | C12-Alkyldiphenyloxide disulfonate | Further components |
| V1.1 | 67.5 | | | 30 | | 2.5 | | | 20 | 0.49 | 0.5 | | |
| V1.2 | | 75 | | 7.5 AS | 7.5 | 10 | | | | | | | 1.5 Sodium lauryl ether sulfate |
| V1.3 | 31.25 | 31.25 | | 7.5 AS | 20 | 10 | | | | | | | 1.5 Sodium lauryl ether sulfate |
| V2.2. | 33.75 | 33.75 | | 30 | | 2.5 | — | — | | 0.6 | 0.5 | | |
| V2.3. | 70 | — | | 30 | | — | — | — | | 0.49 | 0.5 | | |

TABLE 2-continued

Summary of Examples

| Example | Monomers (pphm) | | | | | Other components (pphm) | | | | | | Further components |
|---|---|---|---|---|---|---|---|---|---|---|---|---|
| | EA | BA | EHA | MAS | AM | ASSOC | Malto-dextrin | CMC150 | PVP | 2-EHTG | SDS | C12-Alkyldiphenyloxide disulfonate | |
| B1.1 | 57.5 | | | 30 | 10 | 2.5 | | 20 CMC80 | | | 0.7 | 0.5 | |
| B1.2 | 67.5 | | | 30 | | 2.5 | | 15 | | | 0.49 | 0.5 | |
| B1.3 | 67.5 | | | 30 | | 2.5 | | 10 CMC230 | | | 0.6 | 0.5 | |
| B1.4 | 70 | | | 30 | | | | 20 | | | 0.49 | 0.5 | |
| B1.5 | 67.5 | | | 30 | | 2.5 | | 10 | | | 0.6 | 0.5 | |
| B1.6 | 67.5 | | | 30 | | 2.5 | | 10 | | | 0.6 | 0.5 | 2 alkyl-polyglycoside |
| B1.7 | 67.5 | | | 30 | | 2.5 | | 10 | 5 | | 0.49 | 0.5 | |
| B1.8 | 67.5 | | | 30 | | 2.5 | | 10 | 10 | | 0.6 | 0.5 | |
| B1.9 | 67.5 | | | 30 | | 2.5 Methoxy polyethyleneglycol 1000 methacrylate | | 10 | 5 | | 0.6 | 0.5 | |
| B1.10 | 67.5 | | | 30 | | 2.5 | | 10 | 10 PVP4 | | 1.15 | 0.5 | |
| B1.11 | 33.75 | 33.75 | | 30 | | 2.5 | | 10 | | | 0.6 | 0.5 | |
| B1.12 | 33.75 | | 33.75 | 30 | | 2.5 | | 10 | | | 0.6 | 0.5 | |
| B1.13 | 37 | 37 | | 25 | | 1 | | 10 | | | 0.6 | 0.5 | |
| B2.1 | 34.5 | 34.5 | | 30 | | 1 | | 10 | | | 0.6 | 0.5 | |
| B2.2 | 33.75 | 33.75 | | 30 | | 2.5 | | 10 | | | 0.6 | 0.5 | |
| B3.1 | 33.75 | 33.75 | | 30 | | 2.5 | 10 | 5 | | | | | 1.25 Sodium lauryl ether sulfate |
| B3.2 | 33.75 | 33.75 | | 30 | | 2.5 | 5 | 5 | | | | | 1.25 Sodium lauryl ether sulfate |
| B3.3 | 33.75 | 33.75 | | 30 | | 2.5 | 20 | 5 | | | | | 1.25 Sodium lauryl ether sulfate |
| B3.4 | 33.75 | 33.75 | | 30 | | 2.5 | 20 | 10 | | | | | 1.25 Sodium lauryl ether sulfate |
| B3.5 | 33.75 | 35.25 | | 30 | | 1 | 20 | | | | | | 1.25 Sodium lauryl ether sulfate |
| B4.1. | 31.25 | 31.25 | | 27.5 | | 10 | 20 | — | | | | | 1.5 Sodium lauryl ether sulfate |
| B4.2. | 34.75 | 34.75 | | 30 | | 0.5 | | 12 | | | 0.6 | 0.5 | |
| B5.1 | 30 | 30 | | 40 | | | | 50 CMC80 | | | | | 2 Sodium lauryl ether sulfate 0.2 PETIA |
| B5.2 | 30 | 30 | | 40 | | | | 50 CMC80 | | | | | 2 Sodium lauryl ether sulfate |
| B5.3 | 29.75 | 29.75 | | 40 | | 0.5 | | 50 | | | | | 2 Sodium lauryl ether sulfate |
| B5.4 | 29.75 | 29.75 | | 40 | | 0.5 | | 50 CMC80 | | | | | 2 Sodium lauryl ether sulfate |
| B5.5 | 34.75 | 34.75 | | 30 | | 0.5 | | 12 | | | 0.6 | 0.5 | 0.05 NaPS |
| B5.6 | 34.75 | 34.75 | | 30 | | 0.5 | | 12 | | | 0.6 | 0.5 | 0.025 NaPS |
| B5.7 | 30 | 30 | | 40 | | | | 50 CMC80 | | 0.25 | | | 2 Sodium lauryl ether sulfate |
| B5.8 | 30 | 30 | | 40 | | | | 50 CMC80 | | 0.25 | | | 2 Sodium lauryl ether sulfate 0.2 PETIA |
| B5.9 | 29.75 | 29.75 | | 40 | | 0.5 | | 50 CMC80 | | 0.25 | | | 2 Sodium lauryl ether sulfate |

TABLE 2-continued

Summary of Examples

| Example | Monomers (pphm) | | | | | Other components (pphm) | | | | | | | Further components |
|---|---|---|---|---|---|---|---|---|---|---|---|---|---|
| | EA | BA | EHA | MAS | AM | ASSOC | Malto-dextrin | CMC150 | PVP | 2-EHTG | SDS | C12-Alkyldiphenyloxide disulfonate | |
| B5.10 | 29.94 | 29.94 | | 39.92 | | | | 50 CMC80 | | | | | 2 Sodium lauryl ether sulfate 0.2 BDA2 |
| B5.11 | 30 | 30 | | 40 | | | | 50 CMC80 | | | | | 2 Sodium lauryl ether sulfate 0.2 PETIA |
| B5.12 | 29.75 | 29.75 | | 40 | | 0.5 | | 50 CMC80 | | | | | 2 Sodium lauryl ether sulfate |
| B5.13 | 30 | 30 | | 40 | | | | 50 CMC80 | 0.25 | | | | 2 Sodium lauryl ether sulfate 0.2 PETIA |
| B5.14 | 29.75 | 29.75 | | 40 | | 0.5 | | 50 CMC80 | 0.25 | | | | 2 Sodium lauryl ether sulfate |
| B5.15 | 30 | 30 | | 40 | | | | 100 | | | | | 2 Sodium lauryl ether sulfate 0.2 BDA2 0.5 Acetic acid |
| B5.16 | 30 | 30 | | 40 | | | | 40 | | | | | 2 Sodium lauryl ether sulfate 0.2 BDA2 0.5 Acetic acid |
| B5.17 | 30 | 30 | | 40 | | | | 25 | | | | | 2 Sodium lauryl ether sulfate 0.2 BDA2 0.5 Acetic acid |
| B5.18 | 28.75 | 28.75 | | 40 | | 2.5 | | 50 | | | | | 2 Sodium lauryl ether sulfate 0.2 BDA2 0.5 Acetic acid 0.05 Sodiumhypophpsphite |
| B5.19 | 25 | 25 | | 40 | | 10 | | 50 | | | | | 2 Sodium lauryl ether sulfate 0.2 BDA2 0.5 Acetic acid 0.05 Sodiumhypophpsphite |
| B5.20 | 29.75 | 29.75 | | 40 | | 0.5 | | 100 CMC80 | | | | | 2 Sodium lauryl ether sulfate |
| B5.21 | 30 | 30 | | 40 | | | | 50 CMC80 | 0.1 | | | | 2 Sodium lauryl ether sulfate |
| B5.22 | 34.75 | 34.75 | | 30 | | 0.5 | | 12 | | 0.7 | 0.5 | | 0.1 Trilon B |

Determination of the Viscosity

The viscosity subject to sheer was determined according to DIN 51550, DIN 53018 and DIN 53019 with a Brookfield Viscometer Model RV-03 at 0.3, 1 and 20 rpm (rounds per minute) with spindle Nr. 3 at 20° C.

Determination of Solid Content

The dispersion was dried at 140° C. for 30 minutes and the solid content in % was determined from the ration of dry residue to weighted sample.

Determination of LD-Value

The dispersion was diluted to 0.01% and the light transmission (LD) of the dispersion as compared to pure water as measure for particle size was measured optically with Hach DR/2010.

Determination of Stability of Microcapsules

Under gentle stirring perfume microcapsules (shell: based on melamine-formaldehyde condensate, comprising cationic charged polymer; core: perfume) were added to "Persil® Color" liquid detergent, followed by the inventive rheology modifier (B1.x to B4.x; view table 2); stirring was continued for 30 min. The pH was adjusted again to pH=8. The final formulation was stored at 50° C. for 4 weeks. Sedimentation and/or creaming was judged visually and rated in comparison to a liquid detergent formulation "Persil® Color" (Henkel AG & Co. KGaA, Germany) with perfume microcapsules and rheology modifier (V1.x to V2.x; view table 2) which is not a rheology modifier of the invention (=very bad). The final results are shown in Table 3.

TABLE 3

Properties of the Examples

| Example | LD [%] | Brookfield · Viscosity · 20 rpm 1% ig VE-Water | Viscosity 1% ig liquid detergent formulation | Viscosity mPas In liquid detergent formulation | Microcapsule Stability Test Very bad: --- Very good: ++++ In liquid detergent formulation |
|---|---|---|---|---|---|
| V1.1 | 76 | 990 | | | --- |
| V1.2 | 96 | 20 | | | -- |
| V1.3 | 97 | 15 | | | - |
| V2.2. | 97 | 1020 | | | -- |
| V2.3. | 98 | 150 | | | --- |
| B1.1 | 66 | 515 | | 370 | + |
| B1.2 | 68 | 1020 | 955 | 800 | ++++ |
| B1.3 | 53 | 1200 | | 1485 | +++ |
| B1.4 | 66 | 610 | 1100 | 950 | ++++ |
| B1.5 | 50 | 1070 | 870 | 862 | ++++ |
| B1.6 | 58 | 2150 | 905 | 866 | ++++ |
| B1.7 | 45 | 315 | 490 | 506 | + |
| B1.8 | 48 | 175 | 430 | 954 | ++++ |
| B1.9 | 55 | 530 | 510 | 492 | +++ |
| B1.10 | 48 | 375 | 745 | 742 | +++ |
| B1.11 | 54 | 785 | 1050 | 820 | ++++ |
| B1.12 | 58 | 20 | 700 | 540 | +++ |
| B1.13 | 55 | 230 | | 2190 | ++ |
| B2.1 | 50 | 635 | 860 | 2585 | +++ |
| B2.2 | 57 | 350 | 690 | 1950 | ++ |
| B3.1 | 60 | 525 | 670 | 1690 | +++ |
| B3.2 | 52 | 905 | 810 | 1900 | +++ |
| B3.3 | 49 | 1110 | 670 | 1720 | +++ |
| B3.4 | 50 | 705 | 680 | | |
| B3.5 | 92 | 1015 | 830 | 2410 | ++ |
| B4.1. | 60 | 300 | | | ++ |
| B4.2. | 48 | 1045 | 1560 | 2405 | ++++ |

Determination of Stability of Pigments

For the determination of the pigment stability a premix of 98 g liquid detergent "Persil® Color" (Henkel AG & Co. KGaA, Germany) was poured into a glass vessel. Afterwards 0.1 gram of the pigment powder of "Flamenco Sparkle Gold 220J" or 0.01 gram "Prestige Soft silver" (Sudarshan, particle size 10 μm, bulk density 350 kg/m$^3$), corresponding to 0.1% and 0.01% respectively, was added and gently homogenized for 1 min at about 1500 rpm. In the last formulation step the rheology modifier, as described in table 2 and 4, was added in an amount of 10 gram (20% solid content in aqueous solution), corresponding to 2% solid content in formulation. After additional stirring for 10 min the final liquid detergent formulation in the glass vessel was stored at 50° C. for 4 weeks. After the storage time the creaming and/or sedimentation of the pigments were determined as summarised in table 4 in the following way:

++++ the pigments remain completely homogeneous distributed in the final formulation ---- the pigments are completely phase separated and not at all homogeneously distributed in the final formulation.

The evaluation steps in between are defined by the increasing amount of phase separated pigments.

The final results are shown in Table 4.

TABLE 4

Properties of the Examples

| Example | LD [%] | Brookfield · Viscosity · 1% ig, 20 rpm (mPas) VE-Water | Flamenco Sparkle Gold 220J Stability Test Very bad: --- Very good: ++++ In liquid detergent formulation 2% | Prestige Soft Silver Stability Test Very bad: --- Very good: ++++ In liquid detergent formulation |
|---|---|---|---|---|
| V1.1 | 76 | 990 | --- | n.d. |
| V1.2 | 96 | 20 | --- | n.d. |
| V1.3 | 97 | 15 | --- | --- |
| V2.2. | 97 | 1020 | --- | --- |
| V2.3. | 98 | 150 | --- | --- |
| B5.1 | 92 | 45 | ++++ | ++++ |
| B5.2 | 93 | 45 | +++ | +++ |
| B5.3 | 77 | 65 | ++ | +++ |
| B5.4 | 85 | 55 | +++ | +++ |
| B5.5 | 47 | 575 | ++++ | +++ |
| B5.6 | 43 | 600 | +++ | +++ |
| B5.7 | 89 | 55 | ++ | n.d. |
| B5.8 | 93 | 15 | +++ | n.d. |
| B5.9 | 92 | 15 | ++ | n.d. |
| B5.10 | 92 | 45 | ++++ | n.d. |
| B5.11 | 92 | 45 | +++ | n.d. |
| B5.12 | 86 | 50 | ++ | n.d. |
| B5.13 | 92 | 15 | +++ | n.d. |
| B5.14 | 90 | 20 | ++ | n.d. |
| B5.15 | 95 | 150 | +++ | n.d. |
| B5.16 | 76 | 75 | +++ | n.d. |
| B5.17 | 68 | 50 | ++ | n.d. |
| B5.18 | 79 | 45 | ++ | n.d. |
| B5.19 | 79 | 35 | ++ | n.d. |
| B5.20 | 90 | 25 | ++ | n.d. |
| B5.21 | 92 | 40 | + | n.d. | n.d. = not determined

The invention claimed is:

1. A rheology modifier obtained by polymerizing
   (i) at least one ethylenically unsaturated carboxylic acid;
   (ii) at least one nonionic ethylenically unsaturated surfactant monomer;
   (iii) at least one C$_1$-C$_2$-alkyl methacrylate, and
   (iv) at least one C$_2$-C$_4$-alkyl acrylate, wherein the alkyl chain length averaged over the number of alkyl groups of the alkyl acrylate is 2.1 to 4.0;

in the presence of a separate solvent comprising at least one substituted hydrocarbon selected from the group consisting of substituted and non-substituted oligo- and polysaccharides, substituted and non-substituted β-1,4-D-glucopyranosides, chemically modified or substituted cellulose or combinations thereof.

2. The rheology modifier according to claim 1, wherein the at least one substituted hydrocarbon is selected from the group consisting of carboxymethylcellulose and starch.

3. The rheology modifier according to claim 1, wherein the at least one nonionic ethylenically unsaturated surfactant monomer has the general formula (I)

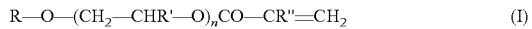

in which R is $C_6$-$C_{30}$-alkyl,
R' is hydrogen or methyl,
R" is hydrogen or methyl, and
n is an integer from 2 to 100.

4. The rheology modifier according to claim 1, wherein the at least one ethylenically unsaturated carboxylic acid is selected from the group consisting of acrylic acid, methacrylic acid, itaconic acid and maleic acid.

5. The rheology modifier according to claim 1, wherein the alkyl acrylate comprises 5 to 85% by weight, based on the total weight of the alkyl acrylate, of copolymerized units of n-butyl acrylate.

6. The rheology modifier according to claim 1, further comprising at least one of an anionic and a nonionic emulsifier.

7. The rheology modifier according to claim 6, wherein the emulsifier has the general formula (II)

wherein R is $C_6$-$C_{30}$-alkyl, R' is hydrogen or methyl,
X is hydrogen or $SO_3M$,
M is hydrogen or an alkali metal, and
n is an integer from 2 to 100.

8. The rheology modifier according to claim 1, wherein the at least one substituted hydrocarbon is present in an amount of 1 to 50% by weight, based on the total weight of the alkyl acrylate.

9. A liquid formulation comprising the rheology modifier as defined in claim 1 and at least one component selected from the group consisting of gas bubbles, nanoparticles, and microcapsules wherein the gas bubbles, nanoparticles, and microcapsules comprise at least one active ingredient selected from the group consisting of enzymes, perfumes, pharmaceuticals, organic particles, pigments, fibers, biocides, herbicides and fungicides.

10. A liquid detergent composition, comprising
at least one rheology modifier as defined in claim 1,
at least one surfactant,
a liquid continuous phase comprising water and
at least one component, dispersed in said liquid continuous phase.

11. The liquid detergent composition according to claim 10, wherein said continuous phase comprises said rheology modifier.

12. The liquid detergent composition according to claim 10 wherein the at least one surfactant comprises at least one anionic surfactant and at least one nonionic surfactant.

13. The liquid detergent composition according to claim 12, wherein the anionic surfactant is comprised in a total amount from 2 to 20 wt. % relative to the liquid detergent composition.

14. The liquid detergent composition according to claim 12, wherein the nonionic surfactant is comprised in a total amount from 1 to 10 wt. % relative to the liquid detergent composition.

15. The liquid detergent composition according to claim 10 further comprising at least one inorganic salt.

16. The liquid detergent composition according to claim 15, wherein the at least one inorganic salt is comprised in a total amount from 0.1 to 1 wt. % relative to the liquid detergent composition.

17. The liquid detergent composition according to claim 10, wherein the at least one component dispersed in the liquid continuous phase particles comprises a particulate solid selected from the group consisting of microcapsules and pigments.

18. The liquid detergent composition according to claim 17, wherein the particulate solid has an average particle size $X_{50,3}$ of from 0.05 to 500 μm.

* * * * *